US010456076B2

(12) United States Patent
Liu

(10) Patent No.: US 10,456,076 B2
(45) Date of Patent: Oct. 29, 2019

(54) METHOD FOR MEASURING MOVEMENT OF CERVICAL VERTEBRA, DEVICE THEREOF AND WEARABLE APPARATUS

(71) Applicant: BOE Technology Group Co., Ltd., Beijing (CN)

(72) Inventor: Xueqiang Liu, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 0 days.

(21) Appl. No.: 14/616,103

(22) Filed: Feb. 6, 2015

(65) Prior Publication Data
US 2016/0157771 A1 Jun. 9, 2016

(30) Foreign Application Priority Data
Dec. 5, 2014 (CN) .......................... 2014 1 0740868

(51) Int. Cl.
*A61B 5/00* (2006.01)
*A61B 5/11* (2006.01)
(Continued)

(52) U.S. Cl.
CPC .......... *A61B 5/4566* (2013.01); *A61B 5/1116* (2013.01); *A61B 5/1121* (2013.01);
(Continued)

(58) Field of Classification Search
CPC .................................................. A61B 5/6814
(Continued)

(56) References Cited

U.S. PATENT DOCUMENTS 4,586,515 A * 5/1986 Berger ................. A61B 5/1121
600/595
4,777,965 A 10/1988 Allison et al.
(Continued)

FOREIGN PATENT DOCUMENTS

CN 1081607 A 2/1994
CN 201131742 Y 10/2008
(Continued)

OTHER PUBLICATIONS

May 9, 2016—(EP)—Extended European Search Report Appn 15155171.0.
(Continued)

*Primary Examiner* — Patrick Fernandes
(74) *Attorney, Agent, or Firm* — Banner & Witcoff, Ltd.

(57) ABSTRACT

Embodiments of the present disclosure provide a method for measuring a movement of the cervical vertebra, a device thereof and a wearable apparatus. The method for measuring a movement of the cervical vertebra comprises: obtaining a movement angle of the cervical vertebra with a sensor; and calculating a movement amount of the cervical vertebra based on the movement angle of the cervical vertebra. Therefore, according to embodiments of the present disclosure, exact data values of the movement angles of the cervical vertebra can be acquired with the sensor, and the movement amount of the cervical vertebra can be calculated on the basis of this, thereby a quantitative value of the movement of the cervical vertebra can be acquired exactly in form of a numerical value, which is convenient for future processings.

8 Claims, 4 Drawing Sheets

(51) Int. Cl.
  *A63B 23/02* (2006.01)
  *A63B 23/025* (2006.01)
(52) U.S. Cl.
  CPC .......... *A61B 5/6803* (2013.01); *A61B 5/6814* (2013.01); *A61B 5/6822* (2013.01); *A61B 5/6831* (2013.01); *A61B 2505/09* (2013.01); *A61B 2562/0219* (2013.01); *A63B 23/025* (2013.01); *A63B 23/0244* (2013.01)
(58) Field of Classification Search
  USPC .................................................. 600/594, 595
  See application file for complete search history.

(56) References Cited

U.S. PATENT DOCUMENTS

| | | | |
|---|---|---|---|
| 4,928,709 A | | 5/1990 | Allison et al. |
| 5,203,346 A | * | 4/1993 | Fuhr .................... A61B 5/1121 |
| | | | 600/594 |
| 5,373,858 A | | 12/1994 | Rose et al. |
| 5,916,181 A | * | 6/1999 | Socci .................... A42B 3/0433 |
| | | | 600/595 |
| 2004/0044293 A1 | * | 3/2004 | Burton .................... A61B 5/18 |
| | | | 600/544 |
| 2006/0251334 A1 | | 11/2006 | Oba et al. |
| 2008/0130553 A1 | * | 6/2008 | Takahashi ............. H04W 12/06 |
| | | | 370/328 |
| 2009/0037135 A1 | * | 2/2009 | Lyndon .................... G01J 5/02 |
| | | | 702/134 |
| 2011/0230792 A1 | * | 9/2011 | Sarig-Bahat ......... A61B 5/1124 |
| | | | 600/595 |
| 2012/0156933 A1 | * | 6/2012 | Kreger ............... A61B 5/02433 |
| | | | 439/625 |
| 2013/0072820 A1 | * | 3/2013 | Lee ..................... G06F 19/3431 |
| | | | 600/594 |
| 2014/0081180 A1 | | 3/2014 | Ghajar |
| 2014/0323921 A1 | | 10/2014 | Huang |

FOREIGN PATENT DOCUMENTS

| | | | | |
|---|---|---|---|---|
| CN | 103876721 A | | 6/2014 | |
| CN | 204293161 U | | 4/2015 | |
| EP | 0092541 A1 | | 10/1983 | |
| EP | 0494749 A1 | | 7/1992 | |
| JP | 10314147 | | 12/1998 | |
| JP | 2001314392 A | | 11/2001 | |
| JP | 2012120648 A | | 6/2012 | |
| JP | 2013188279 A | | 9/2013 | |
| KR | 20140132541 A | | 11/2014 | |
| WO | 9115148 A1 | | 10/1991 | |
| WO | WO199115148 A1 | * | 10/1991 | .......... A61B 5/1121 |
| WO | 2010117714 A1 | | 10/2010 | |
| WO | WO 2010117714 A1 | * | 10/2010 | .......... H04R 1/1041 |

OTHER PUBLICATIONS

Feb. 3, 2016—(CN) Office Action—App 201410740868.5—Eng Tran.
Mar. 16, 2016—(KR) Office Action—App 2015-0070613—Eng Tran.
Beijing Journal of Traditional Chinese Medicine, Jun. 2010, vol. 29, No. 6.
Feb. 25, 2019—(JP) First Office Action Appn 2015-113813 with English Translation.

* cited by examiner

METHOD FOR MEASURING MOVEMENT OF CERVICAL VERTEBRA, DEVICE THEREOF AND WEARABLE APPARATUS

This application claims priority to Chinese Patent Application No. 201410740868.5, filed on Dec. 5, 2014. The present application claims priority to and the benefit of the above-identified application and is incorporated herein in its entirety.

TECHNICAL FIELD

The present disclosure relates to a method for measuring a movement of the cervical vertebra, a device thereof and a wearable apparatus.

BACKGROUND

Currently, with people's increased awareness of health, the harmfulness of the cervical spondylosis is seen more and more. If the cervical vertebra is in an abnormal stable state of extreme anteflexion for a long period of time, the cervical vertebra would be harmed, and such harmfulness is dozens of times severer than that caused by viewing a computer. Currently, however, there is no scheme to perform a quantitative measurement on a movement of the cervical vertebra.

Accordingly, there is needed a scheme capable of measuring a movement of the cervical vertebra.

SUMMARY

In view of this, embodiments of the present disclosure provide a method for measuring a movement of the cervical vertebra, a device thereof and a wearable apparatus, which can measure the movement of the cervical vertebra.

In accordance with one aspect of the present disclosure, there is provided a method for measuring a movement of the cervical vertebra, comprising: obtaining a movement angle of the cervical vertebra with a sensor; and calculating a movement amount of the cervical vertebra based on the movement angle of the cervical vertebra.

In an example, the calculating a movement amount of the cervical vertebra based on the movement angle of the cervical vertebra comprises: acquiring a movement distance corresponding to each of at least one movement angle of the cervical vertebra based on the at least one movement angle of the cervical vertebra; and calculating a sum of the movement distances acquired during a measurement period, as the movement amount of the cervical vertebra.

In an example, the obtaining a movement angle of the cervical vertebra with a sensor comprises: calculating, for each movement of the cervical vertebra, an average velocity of the cervical vertebra corresponding to the movement; and, acquiring the movement angle of the cervical vertebra by multiplying the average velocity with a movement duration of the cervical vertebra.

In an example, the each movement of the cervical vertebra comprises a first motion process and a second motion process which are opposite in direction, and, the method further comprises: calculating a first average velocity corresponding to the first motion process and a second average velocity corresponding to the second motion process; acquiring a first angle by multiplying the first average velocity with a movement duration of the first motion process; acquiring a second angle by multiplying the second average velocity with a movement duration of the second motion process; and determining the angle whose absolute value is greater between the first angle and the second angle as the movement angle of the cervical vertebra for said movement.

In an example, the method further comprises: calculating a valid movement number of the cervical vertebra based on the movement angles of the cervical vertebra.

In an example, the method further comprises: if the movement angle of the cervical vertebra is greater than or equal to a valid movement threshold value, recording said movement of the cervical vertebra as a valid movement of the cervical vertebra; and counting the valid movements of the cervical vertebra during the measurement period, as a valid movement number of the cervical vertebra.

In an example, the at least one movement angle of the cervical vertebra is all movement angles of the cervical vertebra during the measurement period or the valid movement angles of the cervical vertebra during the measurement period.

In an example, the sensor is a three-axis angular velocity sensor, the movement angle of the cervical vertebra comprises at least one of an up-and-down moving angle, a left-and-right horizontal turning angle and a left-and-right flipping angle, the movement amount of the cervical vertebra comprises at least one of an up-and-down moving amount, a left-and-right horizontal turning amount and a left-and-right flipping amount, and, the valid movement number of the cervical vertebra comprises at least one of an up-and-down valid movement number, a left-and-right horizontal turning valid movement number, and a left-and-right flipping valid movement number.

In an example, the method further comprises: providing an alarm to a user when at least one of alarm conditions is met, wherein, the alarm conditions comprise: at least one of the movement amounts of the cervical vertebra is less than its corresponding movement amount threshold value, and at least one of the valid movement numbers of the cervical vertebra is less than its corresponding valid movement number threshold value.

In an example, the method further comprises: performing an authentication as being connected to a host.

In accordance with another aspect of embodiments of the present disclosure, there is further provided a device for measuring a movement of the cervical vertebra, comprising: an obtaining unit configured to obtain a movement angle of the cervical vertebra with a sensor; and a processing unit configured to calculate a movement amount of the cervical vertebra based on the movement angle of the cervical vertebra.

In an example, the processing unit acquires a movement distance corresponding to each of at least one movement angle of the cervical vertebra based on the at least one movement angle of the cervical vertebra, and calculates a sum of movement distances acquired during a measurement period, as the movement amount of the cervical vertebra.

In an example, for each movement of the cervical vertebra, the obtaining unit calculates an average velocity of the cervical vertebra corresponding to the movement, and acquires the movement angle of the cervical vertebra by multiplying the average velocity with a movement duration of the cervical vertebra.

In an example, the each movement of the cervical vertebra comprises a first motion process and a second motion process which are opposite in direction, and, the obtaining unit is further configured to calculate a first average velocity corresponding to the first motion process and a second average velocity corresponding to the second motion process, acquire a first angle by multiplying the first average velocity with a movement duration of the first motion process, acquire a second angle by multiplying the second average velocity with a movement duration of the second motion process, and, determine the angle whose absolute value is greater between the first angle and the second angle as the movement angle of the cervical vertebra for said movement.

In an example, the processing unit further calculates a valid movement number of the cervical vertebra based on the movement angle of the cervical vertebra.

In an example, if the movement angle of the cervical vertebra is greater than or equal to a valid movement threshold value, the processing unit records said movement of the cervical vertebra as a valid movement of the cervical vertebra, and counts the valid movements of the cervical vertebra during the measurement period as a valid movement number of the cervical vertebra.

In an example, the at least one movement angle of the cervical vertebra is all movement angles of the cervical vertebra during the measurement period or the valid movement angles of the cervical vertebra during the measurement period.

In an example, the sensor is a three-axis angular velocity sensor, the movement angles of the cervical vertebra comprise at least one of an up-and-down moving angle, a left-and-right horizontal turning angle and a left-and-right flipping angle, the movement amount of the cervical vertebra comprises at least one of an up-and-down moving amount, a left-and-right horizontal turning amount and a left-and-right flipping amount, and the valid movement number of the cervical vertebra comprises at least one of an up-and-down valid movement number, a left-and-right horizontal turning valid movement number, and a left-and-right flipping valid movement number.

In an example, the device further comprises: a notifying unit configured to provide an alarm to a user when at least one of alarm conditions is met, wherein, the alarm conditions comprise: at least one of the movement amounts of the cervical vertebra is less than its corresponding movement amount threshold value, and at least one of the valid movement numbers of the cervical vertebra is less than its corresponding valid movement number threshold value.

In an example, the device further comprises at least one of the following: an authenticating unit configured to perform an authentication as being connected to a host; a temperature measurement unit configured to measure a temperature of an object to be tested with a total radiation thermometry; and a pedometer unit configured to count steps of the object to be tested.

In an example, the device is a wearable apparatus worn on a head.

In accordance with a further aspect of embodiments of the present disclosure, there is provided a wearable apparatus worn on a head comprising any one of the devices as described above.

Therefore, according to the embodiments of the present disclosure, exact data values of the movement angles of the cervical vertebra can be acquired with the sensor, and the movement amount of the cervical vertebra can be calculated on the basis of this, thereby a quantitative value of the movement of the cervical vertebra can be acquired exactly in form of a numerical value, which is convenient for future processings.

BRIEF DESCRIPTION OF THE DRAWINGS

The present disclosure will be appreciated more easily by referring to following detailed description of the append drawings, in which like reference numbers indicate units of same structure, and in which.

DETAILED DESCRIPTION

Thereafter, solutions of embodiments of the present disclosure will be described clearly and completely in connection with drawings of the embodiments of the present disclosure, but obviously the described embodiments are only some, but not all of the embodiments of the present disclosure. Any other embodiments obtained by those ordinary skilled in the art based on the embodiments of the present disclosure without inventive labors should fall into a scope sought for protection in the present disclosure.

According to the experts, when people lower their heads, an anteflexion limit (i.e., a state in which the chin comes into contact with the sternum) can only be 45°. If a magnitude of the anteflexion reaches up to 30°, the cervical vertebra may be affected. If the cervical vertebra is in an abnormal stable state of extreme anteflexion for a long period of time, the cervical vertebra would be harmed, and such harmfulness is dozens of times severer than that caused by viewing a computer.

Figure 1:
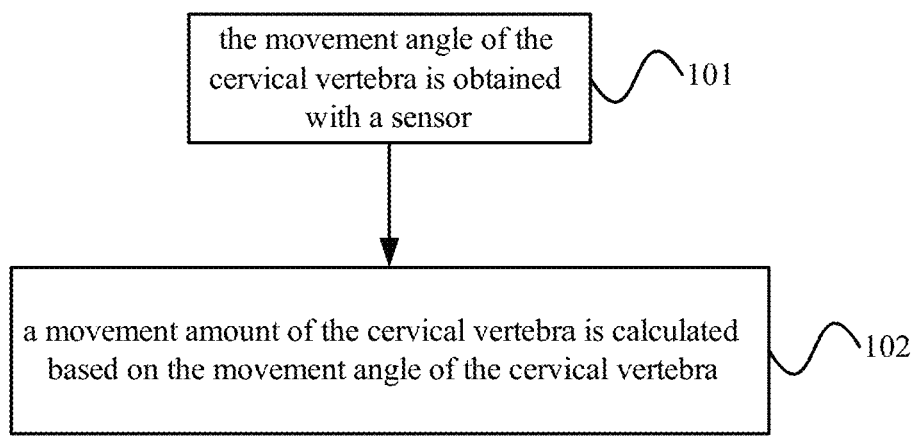
FIG. 1 is a schematic flow diagram illustrating a method for measuring a movement of the cervical vertebra according to an embodiment of the present disclosure.

FIG. 1 is a schematic flow diagram illustrating a method 100 for measuring a movement of the cervical vertebra according to an embodiment of the present disclosure.

As show in FIG. 1, in step 101 of 100, a movement angle of the cervical vertebra is obtained with a sensor, where the movement angle of the cervical vertebra denotes an angle the cervical vertebra is deviated from a main axis; in step 102, a movement amount of the cervical vertebra is calculated based on the movement angle of the cervical vertebra.

Therefore, according to the embodiments of the present disclosure, exact data values of the movement angles of the cervical vertebra can be acquired with the sensor, and the movement amount of the cervical vertebra can be calculated on the basis of this, thereby a quantitative value of the movement of the cervical vertebra can be acquired exactly in form of a numerical value, which is convenient for future processings.

A unit of the movement angle of the cervical vertebra may be degree (°).

In an embodiment of the present disclosure, one movement of the cervical vertebra may indicate a process in which the cervical vertebra starts to move from a starting position in a direction deviating from the starting position, and then after reaching another position, continuous to move in a certainty direction, generally a direction approaching to the starting position, until the cervical vertebra stops moving entirely. It should be noted that, the one movement may also indicate a process in which the cervical vertebra starts to move from the starting position in the direction deviating from the starting position, and then stops moving entirely when reaching the another position; and it may also indicate a process between two movements whose instantaneous velocities are 0, all of the above may be considered as the one movement. In consideration of an integrity of the movement of the cervical vertebra, the present disclosure will be explained with reference to the first situation. The movement angle of the cervical vertebra may indicate a maximum angle made by the cervical vertebra during the one movement of the cervical vertebra. Herein, in the one movement of the cervical vertebra, a position at which the cervical vertebra stops moving entirely may be as same as or different from the starting position. That is, in case of many movements of the cervical vertebra, each starting position may be as same as or different from each other, and the stopping positions may also be as same as or different from each other.

According to an embodiment of the present disclosure, for the each movement of the cervical vertebra, an average velocity of the cervical vertebra corresponding to this movement may be calculated, and the movement angle of the cervical vertebra may be acquired by multiplying the average velocity with a movement duration of the cervical vertebra.

According to an embodiment of the present disclosure, two motion processes which are opposite in direction are included in one movement of a cervical vertebra, thus two angles may be obtained as follows: a first angle from the starting position to the another position and a second angle from the another position to the stopping position. The angle whose absolute value is greater between in the first angle and the second angle is considered as the movement angle of the cervical vertebra of said movement of the cervical vertebra.

The first angle and the second angle may be vectors, and the movement angle of the cervical vertebra may be a scalar. For example, it can be defined that a direction in which the cervical vertebra moves from left to right and a direction in which the cervical vertebra moves from down to up are positive directions, that is, the first angle and the second angle acquired at this point are positive values, and it can also be defined that a direction in which the cervical vertebra moves from right to left and a direction in which the cervical vertebra moves from up to down are negative directions, that is, the first angle and the second angle acquired at this point are negative values. Only absolute values of the first angle and the second angle are compared when the latter are compared, and the maximum absolute value is considered as the movement angle of the cervical vertebra for said movement of the cervical vertebra. It can be appreciated that, when a first valid movement threshold value is utilized to determine whether one movement of the cervical vertebra occurs, it can simply compare the absolute values of the first angle and/or the second angle with the first valid movement threshold value.

When the first angle and the second angle are determined, the starting position and the another position are used as their corresponding reference zero degree position, respectively.

As implemented in practice, the sensor may be an angular velocity sensor. Of course, embodiments of the present disclosure are not limited thereto; it is obvious to those skilled in the art that any other suitable sensors which are available now or to be developed in the future can be utilized to replace the angular velocity sensor.

Hereafter, the embodiments of the present disclosure will be described by taking the angular velocity sensor as an example of the sensor.

The angular velocity sensor can measure an instantaneous velocity (i.e., an instantaneous angular velocity having a unit of: degree/second (°/s)) in real time. Depending on design requirements, the measured instantaneous velocity may be a scalar, and may also be a vector. When the instantaneous velocity is the vector, as described previously, similarly, it can be defined that the instantaneous velocities when the cervical vertebra moves from left to right and when the cervical vertebra moves from down to up are positive values, and it can be defined that the instantaneous velocities when the cervical vertebra moves from right to left and when the cervical vertebra moves from up to down are negative values.

Generally, when people move their cervical vertebras consciously, the cervical vertebra is paused for a moment when it moves to the another position from the starting position as well as returning to the stopping position from the another position. Based on this, by utilizing the angular velocity sensor, movement situations of the cervical vertebra between the two motions which have the same motion directions and whose instantaneous velocities are 0 can be obtained, and in turn movement parameters of the each movement of the cervical vertebra can be acquired.

It is understood that, for the each movement of the cervical vertebra, it is required to perform two measurements of opposite directions. In the each movement of the cervical vertebra, the angular velocity sensor starts measuring the instantaneous velocity of the cervical vertebra in real time since the cervical vertebra starts to move from the starting position in the direction deviating from the starting position, until the instantaneous velocity of the cervical vertebra is equal to 0, that is, the first measurement is finished when the cervical vertebra reaches the another position; and then, the angular velocity sensor starts measuring the instantaneous velocity of the cervical vertebra in real time again since the cervical vertebra starts to move from the another position in an opposite direction (i.e., in the direction approaching to the starting position) until the instantaneous velocity of the cervical vertebra is equal to 0, that is, the second measurement is finished when the cervical vertebra reaches the stopping position.

The first measurement differs from the second measurement only in direction, and hereinafter the description will be described by taking the first measurement as an example.

During the first measurement, the angular velocity sensor can measure and acquire a plurality of instantaneous velocities. Depending on design requirements and actual needs, the plurality of instantaneous velocities may be acquired based on a preset time interval. The angular velocity sensor itself may have a storage function for storing the plurality of instantaneous velocities measured and acquired during the each measurement, or the angular velocity sensor may not store and instead transmit the instantaneous velocities acquired to the outside in real time.

An average velocity of the cervical vertebra may be calculated for the first measurement. The average velocity of the cervical vertebra may be calculated every time when a new instantaneous velocity is obtained, and the average velocity may be an instantaneous average velocity, i.e., an average velocity among the new instantaneous velocity and all previous instantaneous velocities. In an example, by removing the maximum instantaneous velocity and the minimum instantaneous velocity from the plurality of instantaneous velocities currently acquired, an intermediate value in remaining instantaneous velocities may be considered as the average velocity of the cervical vertebra for first measurement. In another example, by removing the maximum instantaneous velocity and the minimum instantaneous velocity from the plurality of instantaneous velocities currently acquired, an average value among the remaining instantaneous velocities may be considered as the average velocity of the cervical vertebra for this movement. Of course, the embodiments of the present disclosure are not limited thereto, and the average velocity of each movement of the cervical vertebra may be calculated according to any other suitable methods. When the instantaneous velocity is the vector, the average velocity during the first measurement is also the vector with the same sign as that of the instantaneous velocity.

Then, a first angle of the movement of the cervical vertebra is acquired by multiplying the average velocity during the first measurement with a movement duration of the cervical vertebra during the first measurement. The movement duration may be obtained via a timer inside or outside the angular velocity sensor.

In fact, it is a very fast process to obtain the average velocity based on the current instantaneous velocity measured by the angular velocity sensor and the instantaneous velocities at various time points which are recorded previously and in turn to acquire a current angle, so the instantaneous average velocity at the each time point may be acquired, and then a current instantaneous movement angle of the cervical vertebra may be acquired by multiplying the instantaneous average velocity with the movement duration of the cervical vertebra up till now during the first measurement. Finally, the angle whose absolute value is the greatest among the plurality of instantaneous movement angles may be considered as the first angle of the movement of the cervical vertebra during the first measurement.

Similarly, the second angle of the movement of the cervical vertebra during the second measurement of opposite direction may be acquired.

Then, by comparing the absolute values of the first angle and the second angle, the absolute value of the angle whose absolute value is greater between they two is determined as the movement angle of the cervical vertebra for this movement of the cervical vertebra.

Furthermore, in order to save a storage space, during the first measurement, only an instantaneous maximum first angle up till now may be recorded and updated in real time, thus during the first measurement what is recorded all the time is the first angle which is maximum instantaneously, and when the first measurement is finished, the stored first angle which is maximum instantaneously is the first angle during the first measurement. Similarly, the second angle during the second measurement may be acquired in this way.

According to an embodiment of the present disclosure, the movement amount of the cervical vertebra may be calculated based on the movements of the cervical vertebra, which will be described in details hereinafter.

The movement amount of the cervical vertebra may be represented by a total movement distance of the cervical vertebra during a predetermined measurement period, such as 1 hour.

The distance may be represented by an arc length. Firstly, the arc length of the each movement is acquired based on the each movement angle. The arc length may be calculated with a following equation (1).

$$L_i = 2\pi r \times (\alpha_i / 360) \qquad \text{equation (1)}$$

Here, i denotes an index of the movement angle of the cervical vertebra measured during the predetermined measurement period, where i is a natural number; $L_i$ denotes the arc length corresponding to the ith movement angle of the cervical vertebra (in unit of: centimeter (cm) or millimeter (mm)); $\alpha_i$ denotes the ith movement angle of the cervical vertebra, which may be a scalar; r denotes a radius of the movement of the cervical vertebra, which may be a preset default value and may have different default values with respect to different crowds such as adults and children. r may be calculated with an equation of (perimeter of the neck/$2\pi$). As for the children, r is about 5 cm, and as for the adults, r is generally not longer than 10 cm, thus generally the default value of r may be within a range from 5 cm to 10 cm.

Afterwards, $$\sum_{i=1}^{n} L_i,$$

i.e., a sum of the movement arc lengths corresponding to the respective movement angles measured during the measurement period is calculated as the movement amount of the cervical vertebra, wherein n is a total number of the movements of the cervical vertebra during the measurement period.

Further, the movement angles may also be utilized to calculate a line segment length (in unit of: centimeter (cm) or millimeter (mm)) on a cervical vertebra motion plane to which the movement of the cervical vertebra is mapped. The line segment length d may be calculated with a following equation (2).

$$d_i = r \sin \alpha_i \qquad \text{equation (2)}$$

wherein, $d_i$ denotes the ith line segment length of the movement of the cervical vertebra during the measurement period, $\alpha_i$ denotes the ith movement angle of the cervical vertebra, and r denotes the radius of the movement of the cervical vertebra.

Afterwards, $$\sum_{i=1}^{n} d_i,$$

i.e., a sum of the line segment lengths corresponding to the respective movement angle measured during the measurement period is calculated as the movement amount of the cervical vertebra, wherein n is the total number of the movements of the cervical vertebra during the measurement period.

According to an embodiment of the present disclosure, the movement amount of the cervical vertebra is a quantitative value acquired by performing measurement on the movement of the cervical vertebra, which may be informed to a user and may also be stored as a piece of historical information for future analysis and usages.

According to one further embodiment, when the header shakes with a little magnitude for many times, although the movement amount of the cervical vertebra is very large, no exercising effect can be achieved for the cervical vertebra, because the magnitude of each movement is too small. Therefore, as for such a case, a valid movement number of the cervical vertebra (i.e., a total number of the movements the cervical vertebra which reach a predetermined magnitude) may also be calculated based on the movement angles of the cervical vertebra $\alpha_i$ according to the embodiments of the present disclosure.

As for one movement of the cervical vertebra, if its movement angle of the cervical vertebra $\alpha_i$ is greater than or equal to a valid movement threshold value, then said movement of the cervical vertebra is recorded as a valid movement of the cervical vertebra. Furthermore, it may also be determined whether the each movement of the cervical vertebra is the valid movement of the cervical vertebra according to whether the distance $L_i$ or $d_i$ is greater than their corresponding valid movement threshold value. Similar to the first valid movement threshold value, this valid movement threshold value may be an empiric value, and may be varied depending on individual conditions.

It is understood that the valid movement threshold value may be set manually.

The unit of the valid movement threshold value may be an angular unit (degree (°)), and may also be a length unit (in unit of: centimeter (cm) or millimeter (mm)). For example, the valid movement threshold value may be within a range from 5° to 15°, for example, may be 10°. For example, in case of radian, the valid movement threshold value may be within a range from 0.5 cm to 2 cm, and in case of the line segment length, the valid movement threshold value may be within a range from 0.5 cm to 3 cm.

And then, the valid movements of the cervical vertebra during the measurement period are counted, as the valid movement number of the cervical vertebra.

According to an embodiment of the present disclosure, the valid movement number of the cervical vertebra is also a quantitative value acquired by performing measurements on the movements of the cervical vertebra, which may be informed to the user separately or together with the movement amount of the cervical vertebra and may also be stored as the historical information for future analysis and usages.

In an example, the movement distance is calculated for each movement angle of the cervical vertebra during the measurement period, and in turn the movement amount of the cervical vertebra is acquired.

Furthermore, in another example, it may determine whether the movement of the cervical vertebra is the valid cervical vertebra movement based on the movement angle of the cervical vertebra whenever the movement angle of the cervical vertebra is acquired, and then the movement distance is calculated only when said movement of the cervical vertebra is the valid cervical vertebra movement, and in turn the movement amount of the cervical vertebra is acquired. In this case, the movement amount of the cervical vertebra is actually the valid movement amount of the cervical vertebra during the measurement period.

In other words, a movement distance corresponding to each of at least one movement angle of the cervical vertebra during the measurement period may be acquired based on the at least one movement angle of the cervical vertebra. The at least one movement angle of the cervical vertebra is all movement angles of the cervical vertebra during the measurement period or the valid movement angles of the cervical vertebra during the measurement period. By calculating the movement distance only when the movement of the cervical vertebra is the valid movement of the cervical vertebra, a calculation amount may be decreased and the storage space may be saved.

According to an embodiment of the present disclosure, besides the left-and-right horizontal turning movement of the cervical vertebra as mentioned previously, the movement of the cervical vertebra may also comprise an up-and-down movement and a left-and-right flipping movement. The up-and-down movement refers to a series of movements composing of lowering the head, returning to the original position and throwing the head back. The left-and-right flipping movement refers to a series of movements composing of the left ear approaching to the left shoulder, returning to the original position and the right ear approaching to the right shoulder on the premise of facing forward. Therefore, it can be seen that the left-and-right horizontal turning movement, the up-and-down movement and the left-and-right flipping movement are movements surrounding three axes where any two of the three axes are perpendicular with each other.

According to an embodiment of the present disclosure, the angular velocity sensor may be a three-axis angular velocity sensor to obtain the angles in the above three movements.

Thus, accordingly, the movement angles of the cervical vertebra may comprise at least one of an up-and-down moving angle, a left-and-right horizontal turning angle and a left-and-right flipping angle, The movement amount of the cervical vertebra comprises at least one of an up-and-down moving amount, a left-and-right horizontal turning amount and a left-and-right flipping amount, and the valid movement number of the cervical vertebra comprises at least one of an up-and-down valid movement number, a left-and-right horizontal turning valid movement number, and a left-and-right flipping valid movement number.

It is understood that the first/valid movement threshold value may have identical or different values with respect to the different movement directions.

Furthermore, since the movement amount of the cervical vertebra and the valid movement number of the cervical vertebra may be used to indicate a status of the movements of the cervical vertebra in the predetermined time period, whether to provide an alarm to the user may be determined in order to prompt that the user needs to move his/her cervical vertebra in an embodiment of the present disclosure.

In an example, the alarm is provided to the user when at least one of following alarm conditions is met:
at least one of the movement amounts of the cervical vertebra is less than the corresponding movement amount threshold value; and
at least one of the valid movement numbers of the cervical vertebra is less than the corresponding valid movement number threshold value.

The movement amount threshold value and the valid movement threshold value may have identical or different values respectively with respect to different motions of the cervical vertebra. The movement amount threshold value, the first/valid movement threshold value and the valid movement number threshold value may be set manually according to experiences or individual conditions.

Of course, as needed, it may configure that an alarm indicating that the cervical vertebra moves too much is provided to the user=when the movement amount and/or the valid movement number of the cervical vertebra exceed another threshold value.

The method 100 according to the embodiment of the present disclosure may be implemented in a wearable apparatus, and the alarm may be provided to the user in a form of sounds and/or vibrations. Therefore, as compared with a conventional reminding mode which is only based on an alarm clock timing and does not perform any measurements on the movements of the cervical vertebra, the alarm according to the embodiments of the present disclosure is more targeted due to the measurements directed to the movements of the cervical vertebra, and the alarm modes with the sounds and/or vibrations are more likely to draw the user's attention, thus a more efficient reminder is achieved.

Figure 2:
FIG. 2 illustrates one example of a wearable apparatus.

For example, the wearable apparatus may be a headband, a hairband, a respirator, a mask, an ear muff, and a wind resistant facecloth etc., which may be worn by the head. One example of the wearable apparatus is shown in FIG. 2, wherein the wearable apparatus is a headband.

Furthermore, Bluetooth devices or RFID (radio frequency identification) tags may also be utilized to perform an authentication.

Furthermore, because the results of the above measurement and calculation may be stored or transmitted externally, an identity of the user may be authenticated before measuring the movement angle of the cervical vertebra in order to protect user's privacy. Any suitable methods may be used by those skilled in the art to perform the authentication process, which will not be repeated here in order to avoid obscuring the present disclosure.

Of course, in the method 100 for measuring the movement of the cervical vertebra according to the embodiment of the present disclosure as describe above, hardware and/or software may be utilized as appropriate to perform process such as a filtering on data to remove noise etc. The detailed description thereof will be omitted here so as to avoid obscuring the present disclosure.

Figure 3:
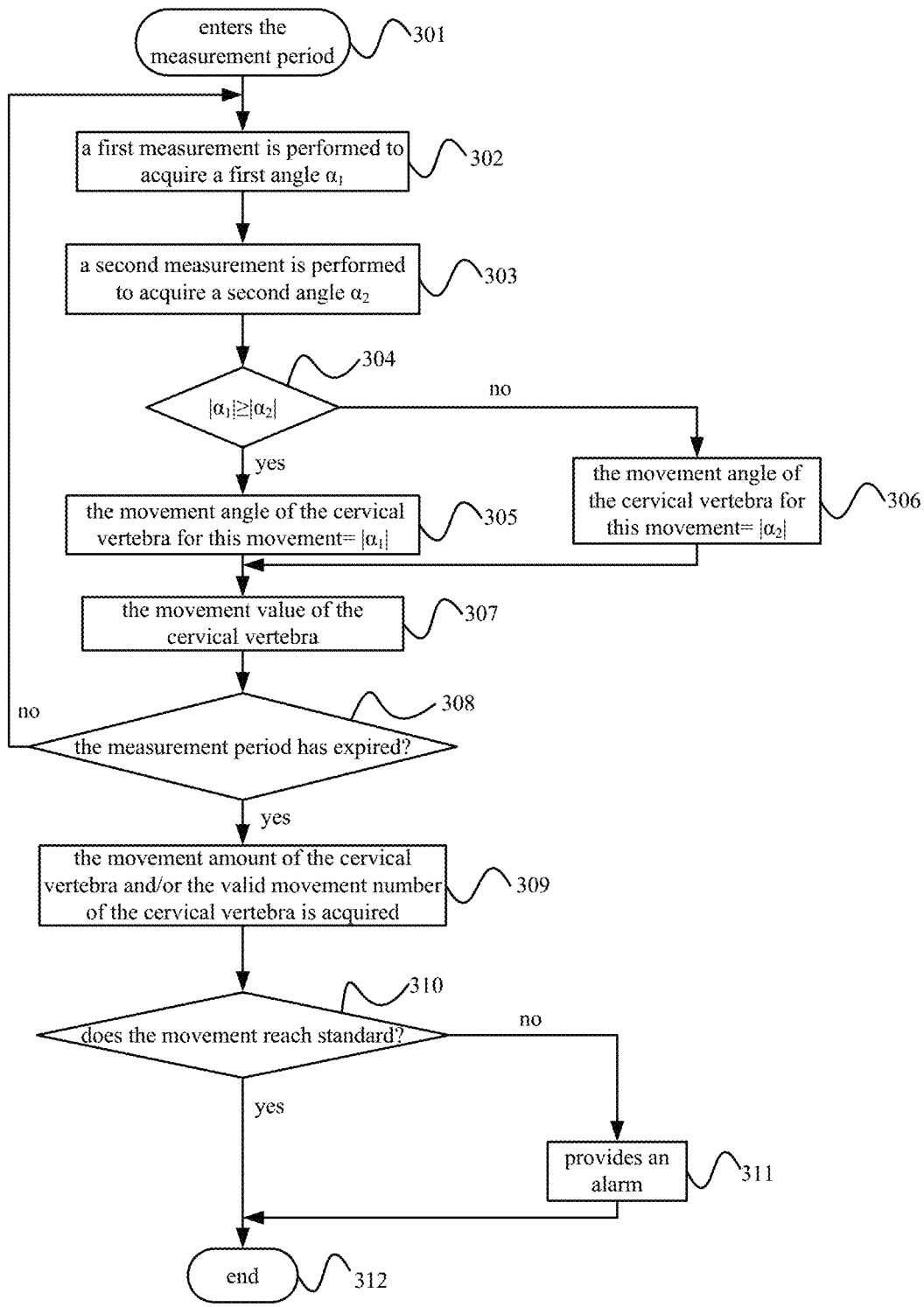
FIG. 3 illustrates an exemplary flow diagram of a method of one specific implementation according to the embodiment of the present disclosure.

FIG. 3 illustrates an exemplary flow diagram of a method 300 of one specific implementation according to an embodiment of the present disclosure. It will be understood that, the flow diagram shown in FIG. 3 are only for schematic illustration, however the embodiments of the present disclosure are not limited thereto, and those skilled in the art may add, modify, delete and replace any one steps therein according to design requirements and actual situations.

As show in FIG. 3, in step 301 of method 300, the measurement period begins. For example, the measurement period is 1 hour, that is, periodic measurements may be performed by taking the 1 hour as the measurement period.

In step 302, the first measurement is performed for the each movement of the cervical vertebra to acquire the first angle $\alpha_1$.

In step 303, the second measurement is performed to acquire the second angle $\alpha_2$.

Then, in step 304, a comparison is performed to determine whether the absolute value of the first angle $\alpha_1$ is greater than or equal to the absolute value of the second angle $\alpha_2$.

If the absolute value of the first angle $\alpha_1$ is greater than or equal to the absolute value of the second angle $\alpha_2$, then the process goes to step 305. In step 305, the movement angle of the cervical vertebra for this movement is determined as the first angle $\alpha 1$.

Otherwise, if the absolute value of the first angle $\alpha_1$ is less than the absolute value of the second angle $\alpha_2$, then the process goes to step 306. In step 306, the movement angle of the cervical vertebra for this movement is determined as the second angle $\alpha_2$.

The processes for obtaining the first angle $\alpha_1$ and the second angle $\alpha_2$ have been described in detail previously, which will not be repeated here.

Then in step 307, a value of the movement of the cervical vertebra (i.e., the movement distance $L_i$ or $d_i$) is obtained based on the movement angles of the cervical vertebra. Of course, a determination whether the movement of the cervical vertebra is the valid movement of the cervical vertebra may be further made here.

Then in step 308, it is decided whether the measurement period has expired.

If the measurement period has not expired, then the process returns back to step 302 to continue to measure the next movement of the cervical vertebra. Otherwise, if the measurement period has expired, then the process goes to step 309.

In step 309, the movement amount of the cervical vertebra and/or the valid movement number of the cervical vertebra during the measurement period is obtained. As described previously, the sum of the movement distances of the cervical vertebra during the measurement period may be obtained as the movement amount of the cervical vertebra.

Next, in step 310, it is decided whether the movement amount of the cervical vertebra and/or the valid movement number of the cervical vertebra is greater than or equal to their corresponding threshold values according to the aforementioned conditions.

When only one of the movement amount of the cervical vertebra and the valid movement number of the cervical vertebra is obtained, if the obtained value is greater than or equal to its corresponding threshold value, then it is deemed that the movement of the cervical vertebra during the measurement period reaches its standard. When both the movement amount of the cervical vertebra and the valid movement number of the cervical vertebra are obtained, only if both of them are greater than or equal to their corresponding threshold values, it is deemed that the movement of the cervical vertebra during the measurement period reaches the standard.

If it is decided that the movement of the cervical vertebra during the measurement period has not reached the standard, then the alarm is provided to the user in step 311.

Otherwise, if it is decided that the movement of the cervical vertebra during the measurement period has reached the standard, then the process is terminated in step 312.

Obviously, the method 300 according to the embodiment of the present disclosure may also be implemented in the wearable apparatus.

Figure 4:
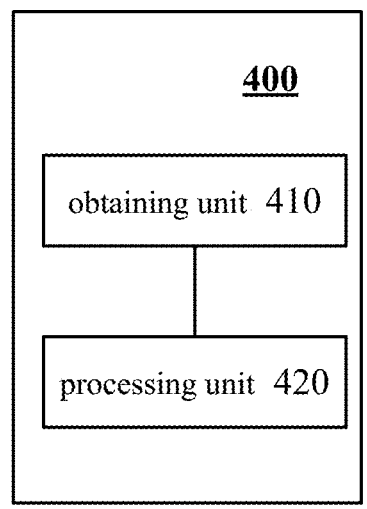
FIG. 4 illustrates a schematic block diagram of a device for measuring a movement of the cervical vertebra according to an embodiment of the present disclosure.

FIG. 4 illustrates a schematic block diagram of a device 400 for measuring a movement of the cervical vertebra according to an embodiment of the present disclosure.

As show in FIG. 4, the device 300 may comprise an obtaining unit 410 and a processing unit 420.

The obtaining unit 410 is configured to obtain a movement angle of the cervical vertebra with a sensor. The processing unit 420 is configured to calculate a movement amount of the cervical vertebra based on the movement angle of the cervical vertebra.

Therefore, according to embodiments of the present disclosure, exact data values of the movement angles of the cervical vertebra can be acquired with the sensor, and the movement amount of the cervical vertebra can be calculated on the basis of this, thereby a quantitative value of the movement of the cervical vertebra can be acquired exactly in form of a numerical value, which is convenient for future processings.

The sensor may be arranged inside the obtaining unit 410. Furthermore, as will be appreciated by those skilled in the art, the obtaining unit 410 and the processing unit 420 may be divided physically, or may only be divided logically, therefore, as implemented in practical, the device 400 may comprise a sensor and a microcontroller Unit (MCU), and the MCU may implement all or part of the remaining functions other than the function of sensing the velocity of the cervical vertebra movement. That is to say, the MCU may be utilized to implement functions for calculating the average velocity of each movement of the cervical vertebra, calculating the movement angle of the each movement, calculating of the movement distance, acquiring the valid movement number of the cervical vertebra and so on. By utilizing a high-performance MCU, a size of the device 400 may be further decreased, thereby a miniaturization is realized.

Of course, the embodiments of the present disclosure are not limited thereto, and the device 400 may also comprise any other necessary devices which are not shown in the present disclosure.

Specifically, for the each movement of the cervical vertebra, the obtaining unit 410 calculates the average velocity of the cervical vertebra, and acquires the movement angle of the cervical vertebra by multiplying the average velocity with the movement duration of the cervical vertebra.

In an example, by removing the maximum instantaneous velocity and the minimum instantaneous velocity from the acquired plurality of instantaneous velocities, an intermediate value in remaining instantaneous velocities is considered as the average velocity of the cervical vertebra for this movement. In another example, by removing the maximum instantaneous velocity and the minimum instantaneous velocity from the acquired plurality of instantaneous velocities, an average value among the remaining instantaneous velocities may be considered as the average velocity of the cervical vertebra for this movement. Of course, the embodiments of the present disclosure are not limited thereto, and the average velocity of the each movement of the cervical vertebra may be calculated according to any other suitable methods.

Hereafter, the processing unit 420 acquires the movement angle of the cervical vertebra as mentioned previously, and acquires the movement amount of the cervical vertebra based on the each movement angle. Furthermore, the processing unit 420 may also acquire the valid movement number of the cervical vertebra based on the each movement angle.

The processes of calculating the movement amount of the cervical vertebra and the valid movement number of the cervical vertebra have been described in detail previously, so the processes will not be repeated here.

As previously mentioned, when the sensor is the three-axis angular velocity sensor, the movement angles of the cervical vertebra comprise at least one of an up-and-down moving angle, a left-and-right horizontal turning angle and a left-and-right flipping angle, the movement amount of the cervical vertebra comprises at least one of an up-and-down moving amount, a left-and-right horizontal turning amount and a left-and-right flipping amount, and the valid movement number of the cervical vertebra comprises at least one of an up-and-down valid movement number, a left-and-right horizontal turning valid movement number, and a left-and-right flipping valid movement number.

Furthermore, in order to prompt that the user needs to move his/her cervical vertebra, the device 400 further comprises: a notifying unit (not shown) configured to providing an alarm to the user when at least one of alarm conditions is met, that is, when at least one of the movement amounts of the cervical vertebra is less than its corresponding movement amount threshold value or at least one of the valid movement numbers of the cervical vertebra is less than its corresponding valid movement number threshold value, the notifying unit may provide the alarm to the user with sounds or vibrations.

In this way, as compared with a conventional reminding mode which is only based on an alarm clock timing and does not perform any measurements on the movements of the cervical vertebra, the alarm according to the embodiments of the present disclosure is more targeted due to the measurements directed to the movements of the cervical vertebra, and the alarm modes with the sounds and/or vibrations are more likely to draw the user's attention, thus a more efficient reminder is achieved.

Furthermore, the device 400 may also comprise: an authenticating unit (not shown) configured to perform an authentication as being connected to a host. Here, Bluetooth devices or RFID (radio frequency identification) tags may be utilized to perform the authentication.

In an example, the device 400 further comprises: a pedometer unit (not shown) configured to count steps of an object to be tested.

Generally, a conventional pedometer such as sports watch may be worn on a wrist, however, a disadvantage is in that the step-counting is not exact. A result of the step-counting would be interred greatly in a process where human arms are shaking or the body is moving (especially when the hand moves irregularly), so the effect of the step-counting is poor, especially in the process of running, the deviation is larger. Thus the deviations between physiological parameters (for example, consumed calories) indices and the actual numerical value are large.

The device 400 according to the embodiment of the present disclosure may be implemented as a wearable apparatus worn on the head. Since the human's head generally remains stabilized with respect the body in motion, and even if the header moves, the magnitude of the motion is far less than that of the arm shaking, the user's actual steps can be reflected actually, thereby exact physiological parameter indices are acquired.

Specifically, the three-axis sensor is utilized by the pedometer unit in the device 400 to implement a step-counting function. The principle of performing the step-counting by utilizing the three-axis sensor will be described hereinafter with reference to FIG. 5 and FIG. 6.

Figure 5:
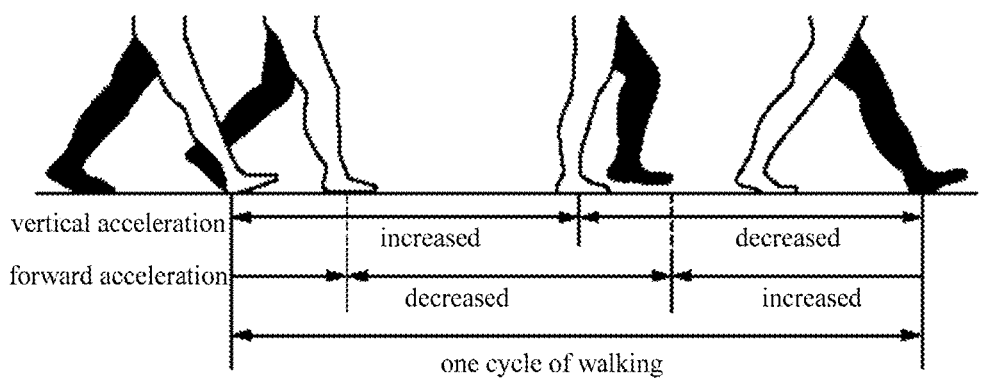
FIG. 5 illustrates one schematic view when a human body is going forward.
Figure 6:
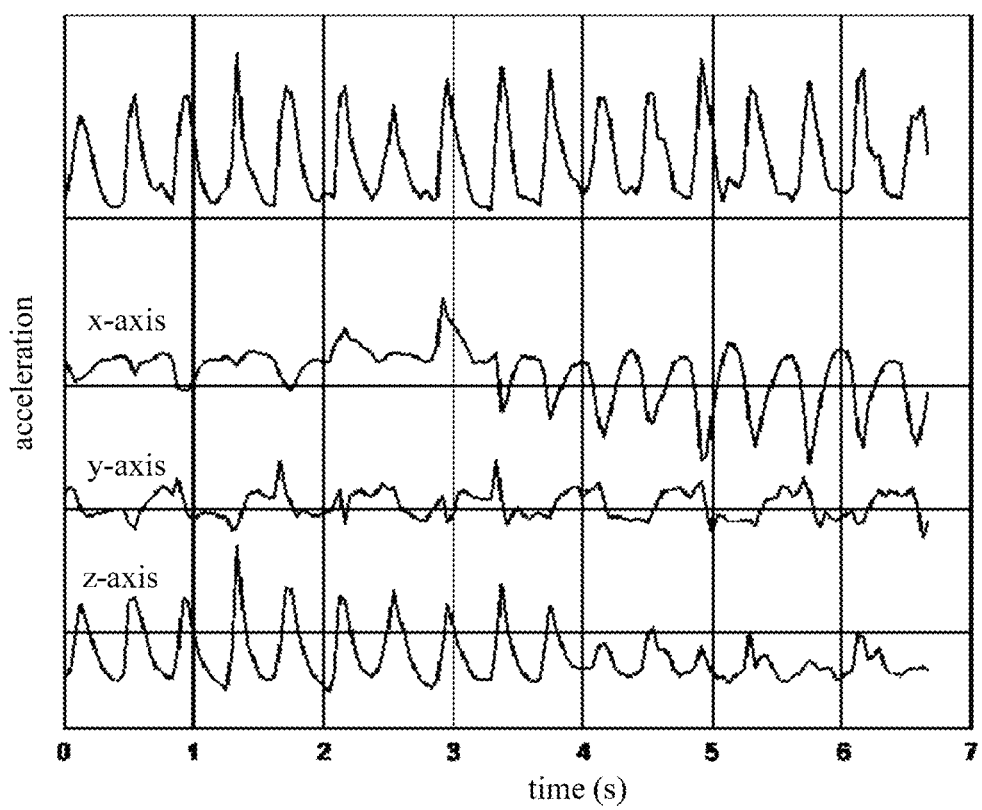
FIG. 6 illustrates accelerations sensed with a three-axis sensor.

FIG. 5 illustrates one schematic view when a human body is going forward, and FIG. 6 illustrates the acceleration sensed by utilizing a three-axis sensor.

As show in FIG. 5, in a horizontal walking movement, two accelerations of vertical direction and forward direction vary periodically. Specifically, in an action of recovering a leg during the walking, since a gravity centre uplifts and a single foot touches the ground, the acceleration of vertical direction increases positively, and afterwards as going ahead, the gravity centre shifts down and both feet touch the ground, and the acceleration is reversed. The horizontal acceleration decreases when a leg is recovered and increases when taking a step.

Referring to FIG. 6, it can be seen that in the walking movement, curves of the accelerations generated in vertical axis (x-axis) and a forward axis (y-axis) versus time are approximately sinusoidal curves, and a peak occurs at a certain point, wherein the acceleration in the vertical direction varies the most; by performing a detection and a calculation as well as an acceleration threshold value decision on the peaks in the track, a step number of user's motion may be counted in real time, and the user's walking distance may be further estimated accordingly. Z-axis denotes the acceleration in left-and-right direction.

Then a sinusoidal curve track of the walking movement can be obtained via the three-axis sensor.

And then a peak detection is performed. A vector length and a motion direction of the last motion are recorded; the direction of the current acceleration may be decided based on the variance in the vector lengths and compared with the previously saved acceleration direction; if the direction of the current acceleration is reversed, it is indicated that a peak value state is just past, then a step-counting logic is used to perform the step-counting, otherwise it is discarded. The steps in user's walking may be acquired by counting the number of the peaks.

Accordingly, according to the embodiment of the present disclosure, the pedometer unit is disposed in the device wearable on the head, since the human's head remains stabilized with respect the body in motion and even if the header moves, the magnitude of the motion is far less than that of the arm shaking, the user's actual steps can be reflected actually, thereby exact physiological parameter indices may be acquired and thus the resulting step-counting result is more accurate.

Furthermore, a forehead temperature is also an important index of the physiological parameter, and in the conventional method, a forehead temperature gun is targeted to the head area to perform scanning; however, a volume of the forehead temperature gun is too large and not suitable for a measurement under a motion state. Considering a case that a body temperature of a human body may rise up to an abnormal value when being at work or doing sports, the device 300 may also comprise: a temperature measurement unit (not shown) configured to measure the temperature of the object to be tested by utilizing a total radiation thermometry. And when the body temperature of the human body is acquired through the measurement go beyond a secure range, the alarming may be performed by the notifying unit. The temperature of the object to be tested is measured with the total radiation thermometry, so that the volume of the device 300 is smaller and the forehead temperature can be calculated exactly, thus the user knows his/her forehead temperature more conveniently and quickly.

According to different temperature measurement theories, there are generally three methods for designing an infrared thermometer: a total radiation thermometry for determining the radiation temperature of an object by measuring a thermal radiation of full wavelength irradiating to the object; a radiance thermometry for determining the brightness temperature of the object by measuring the monochromatic radiation brightness when the object is under a thermal radiation of certain wavelength; and a colorimetry method for determining the temperature of the object to be tested based on the variance of the ratio of monochromatic radiation brightness when the object is under thermal radiations of two wavelengths with the temperature.

The radiance thermometry can be performed without any ambient-temperature compensations, its emissivity error is small, and a temperature measurement accuracy is high, however it operates in a short wave area and is only suitable for a high temperature measurement. The optical system of the colorimetry method can be occluded partially, is affected slightly by the smog and the dust, and the temperature measurement error is small, however, proper wave bands must be selected so that the difference among the emissivity of the wave bands is small.

In the embodiment of the present disclosure, the total radiation thermometry is employed to calculate the temperature of the object to be tested. With the total radiation thermometry, the temperature is determined according to the total radiation in all wavelength range, thus the radiation temperature of the object is acquired. Such a method is chosen because a wavelength of an object in medium and low temperature is large, and the radiated signal is rather weak; furthermore, the corresponding device is of simple structure and lower cost. Hereafter, the theory of the total radiation thermometry will be explained simply.

A relational expression between a radiator temperature and a detection voltage, i.e., equation (3) can be derived from the Planck formula.

$$V = Ra\varepsilon\sigma T^4 = KT^4 \qquad \text{equation (3)}$$

In equation (3), $K=Ra\varepsilon\sigma$, for example, $\varepsilon$ takes the value of 1, which is determined by experiment, T denotes an absolute temperature of the object to be tested, R denotes a detector sensitivity, a denotes a constant pertaining to the atmospheric attenuation distance, $\varepsilon$ denotes the radiance, and $\sigma$ denotes a Stephanian_Boltzmann constant.

Therefore, the temperature of the object to be tested may be determined by the detection voltage, the equation (3) shows that an output signal of the detector has a nonlinear relation with the temperature of the object, and V is proportional to a fourth power of T, so a linearization process needs to be performed. After the linearization process, the apparent temperature of the object is acquired which needs to be subjected to radiance correction to become a true temperature, its correction formula is as follows:

wherein Tr is the radiation temperature (apparent temperature) $\varepsilon(T)$ is the radiance which takes a value in range from 0.1 to 0.9.

Due to an affection of the radiated signal of modulator piece, the true temperature after the radiance correction is higher than a environmental temperature and needs to be subjected to an environmental temperature compensation, that is, the actual temperature of the object to be tested can be acquired finally by adding the environmental temperature to the true temperature.

The total radiation thermometry is utilized so that the size of the device 300 is minimized, and the temperature result with an accuracy of 0.1~0.2 may be acquired, which may meet daily needs fully.

Furthermore, when the temperature result is greater than 37.5° C., an alarm may be provided to the user by the notifying unit with the sounds and/or vibrations.

In another example, hardware and/or software filtering may be performed on the acquired data (the cervical vertebra movement amount, the step-counting data and the temperature value) whenever appropriate to remove the interference data therein.

For example, regarding the result of the step-counting, a handheld device may undergo some twitching states with small magnitudes and fast speed (known as "hand shaking"), or a user who makes a prank wants to simulate human walking by means of shaking the device quickly and repeatedly in a short time, and if such interference data is not removed, the exact value of step-counting will be affected. Such interference may be filtered by detection along with threshold value and stride frequency decision. Generally, the maximum frequency of human running is 5 HZ, that is, the time interval between two adjacent steps is at least greater than 0.2 second, therefore high frequency noises may be filtered by setting a maximum threshold value for the time interval in the step-counting process, that is, the instances with too high stride frequency may be removed. Also, a certain threshold value may be set to be compared with the last acceleration to decide whether the motion belongs to a valid motion, and only a valid motion may be counted in the step-counting process.

According to another embodiment of the present disclosure, there is further provided a wearable apparatus worn on the head, which comprises the device 400 as described above.

Accordingly, according to embodiments of the present disclosure, the wearable apparatus has functions of measuring a movement of the cervical vertebra, step-counting and temperature measurement simultaneously. Exact data values of the movement angles of the cervical vertebra can be acquired with the sensor, and the movement amount of the cervical vertebra can be calculated on the basis of this, thereby a quantitative value of the movement of the cervical vertebra can be acquired exactly in form of a numerical value, which is convenient for future processings. Furthermore, since the human head remains stabilized with respect the body in motion and even if the header moves, the magnitude of the motion is far less than that of the arm shaking, then the user's actual steps can be reflected actually, thereby exact physiological parameter indices may be acquired by the wearable apparatus. In addition, the size of the wearable apparatus is minimized, and the temperature result with an accuracy of 0.1~0.2 may be acquired, which may meet daily needs fully.

It is to be noted that, only the parts pertaining to the embodiments of the present disclosure are shown in the appended drawings for clarity and concise, however, it should be understood by those skilled in the art that the devices or apparatuses shown in the append drawings may comprise other necessary units.

Those skilled in the art should realize that various units or parts described with reference to the embodiments of the present disclosure may be implemented in a form of electronic hardware, computer software or combination thereof, and components or steps of the embodiments of the present disclosure have been described generally in term of functions so as to clearly illustrate interchangeability between a hardware implementation and a software implementation. Whether one of functions is implemented in the form of hardware or in the form of software is dependent on a particular application to which the technical solution is applied and particular design constraints. For each specific application, different methods may be used by professionals to achieve the described functionality, but such implementation should not be construed as exceeding the scope of the present disclosure.

For the purpose of convenience and simplicity of the description, it is clear that those skilled in the art can easily understand the particular processes of the systems, apparatus and units therein as described above with reference to the corresponding processes in the embodiments of the method described hereinbefore, and the detailed thereof is omitted.

It should be understood from the embodiments provided in the present disclosure that the disclosed systems and apparatus can be implemented in other ways. For example, the above-described device embodiments are merely illustrative in nature, such as the division of the units, just is a logic function division, and another division manner may be adopted in an actual implementation, for example a plurality of units or components may be combined or can be integrated into another system, or some of the features can be ignored or not performed. In addition, mutual coupling or direct coupling or communication connection discussed above may be an indirectly coupling or a communication connection via a number of interfaces, devices or units, an may be electrical, mechanical, or other form.

Units described as separate members may be or may not be physically separated, and components shown as a cell may be or may not be physical units, either can be located in a place, or can be distributed to a plurality of network units. According to the actual requirements, part or all of the units can be selected to achieve the purpose of the technical solution of the present disclosure.

Furthermore, the individual functional units in various embodiments of the present disclosure may be integrated into one processing unit, or each unit may be a separate physical presence, or two or more units may be integrated into a single unit. The integrated units can be implemented both in the form of hardware and in the form of software function units.

Said integrated unit can be stored in a computer readable storage medium when it is implemented in the form of software function units and is sold or used as an independent product. Based on this understanding, the technical solution of the present disclosure in essence or the part of the technical solution contributing to the prior art of the technical solution, or all or part of the technical solution may be embodied in the form of software products, the computer software product is stored in a storage medium and includes instructions for making a computer device (may be a personal computer, a server, or network equipment) to perform all or part of steps of the method as provided in the various embodiments of the present invention. The storage medium may include: U disk, mobile hard disk, Read-Only Memory (ROM), a Random Access Memory (RAM), magnetic disk, or CD-ROM, and other media capable of storing program codes Above are only specific embodiments of the present disclosure, and the scope of the present disclosure is not so limited. Any ordinary person skilled in the art may easily make various modifications and alterations, and it is intended that all these modifications and alterations should be encompassed within the appended claims. Therefore, the scope of the present disclosure should be defined by the appended claims.

What is claimed is:

1. A device for measuring a movement of a cervical vertebra, comprising:
 a sensor configured to sense a corresponding plurality of movement angles of the cervical vertebra for a plurality of movements of the cervical vertebra during a predetermined measurement period, wherein each of the plurality of movements of the cervical vertebra comprises a first motion process and a second motion process which have inverse directions and whose starting instantaneous velocities and stopping instantaneous velocities are both zero;
 a microcontroller unit comprising:
  an obtaining unit configured to obtain the plurality of movement angles of the cervical vertebra sensed by the sensor, wherein each of the plurality of movement angles of the cervical vertebra is an angle whose absolute value is greater between a first angle which is a maximum angle made by the cervical vertebra during the first motion process and a second angle which is a maximum angle made by the cervical vertebra during the second motion process during a corresponding one of the plurality of movements of the cervical vertebra, and
  a processing unit configured to calculate a movement total amount of the cervical vertebra during the predetermined measurement period based on the plurality of movement angles of the cervical vertebra,
  wherein, the processing unit acquires a plurality of movement arc lengths, each being corresponding to one of the plurality of movements of the cervical vertebra and determined based on a corresponding one of the plurality of movement angles of the cervical vertebra corresponding to the one of the plurality of movements of the cervical vertebra, and accumulates a sum of the plurality of movement arc lengths for the plurality of movements of the cervical vertebra acquired during the predetermined measurement period as the movement total amount of the cervical vertebra; and a notifying unit configured to provide an alarm to a user by sounds or vibrations for prompting that the user needs to move the cervical vertebra when the movement total amount of the cervical vertebra during the predetermined measurement period is less than a predetermined threshold value of the movement amount, wherein, if a movement angle among the plurality of movement angles of the cervical vertebra is greater than or equal to a valid movement threshold value, the processing unit records the corresponding one of the plurality of movements of the cervical vertebra as a valid movement of the cervical vertebra, and counts the valid movements of the cervical vertebra during the measurement period as a valid movement number of the cervical vertebra.

2. The device as claimed in claim 1, wherein, for each movement of the cervical vertebra, the obtaining unit calculates an average velocity of the cervical vertebra corresponding to said each movement, and acquires a corresponding one of the plurality of movement angles of the cervical vertebra by multiplying the average velocity with a movement duration of the cervical vertebra.

3. The device as claimed in claim 2, wherein, the obtaining unit is further configured to calculate a first average velocity corresponding to the first motion process and a second average velocity corresponding to the second motion process, acquire the first angle by multiplying the first average velocity with a movement duration of the first motion process, acquire the second angle by multiplying the second average velocity with a movement duration of the second motion process, and, determine one of the first angle and the second angle as the corresponding one of the plurality of movement angles of the cervical vertebra for said each movement based on which of the first angle and the second angle has a greater absolute value.

4. The device as claimed in claim 1, wherein, the sensor is a three-axis angular velocity sensor,
the movement angle among the plurality of movement angles of the cervical vertebra comprises at least one of an up-and-down moving angle, a left-and-right horizontal turning angle and a left-and-right flipping angle,
the movement amount of the cervical vertebra comprises at least one of an up-and-down moving amount, a left-and-right horizontal turning amount and a left-and-right flipping amount, and
the valid movement number of the cervical vertebra comprises at least one of an up-and-down valid movement number, a left-and-right horizontal turning valid movement number, and a left-and-right flipping valid movement number.

5. The device as claimed in claim 1, wherein the device further comprises at least one of the following:
an authenticating unit configured to perform an authentication to be connected to a host;
a temperature measurement unit configured to measure a temperature of an object to be tested by utilizing a total radiation thermometry; and
a pedometer unit configured to count steps of the object to be tested.

6. The device as claimed in claim 1, wherein the device is included in a wearable apparatus worn on a head.

7. A wearable apparatus worn on a head, comprising a device for measuring a movement of a cervical vertebra, wherein the device comprises:
a sensor configured to sensing a corresponding plurality of movement angles of the cervical vertebra for a plurality of movements of the cervical vertebra during a predetermined measurement period, wherein each of the plurality of movements of the cervical vertebra comprises a first motion process and a second motion process which have inverse directions and whose starting instantaneous velocities and stopping instantaneous velocities are both zero;
a microcontroller unit comprising:
an obtaining unit configured to obtain the plurality of movement angles of the cervical vertebra sensed by the sensor, wherein each of the plurality of movement angles of the cervical vertebra is an angle whose absolute value is greater between a first angle which is a maximum angle made by the cervical vertebra during the first motion process and a second angle which is a maximum angle made by the cervical vertebra during the second motion process during a corresponding one of the plurality of movements of the cervical vertebra, and
a processing unit configured to calculate a movement total amount of the cervical vertebra during the predetermined measurement period based on the plurality of movement angles of the cervical vertebra,
wherein, the processing unit acquires a plurality of movement arc lengths, each being corresponding to one of the plurality of movements of the cervical vertebra and determined based on a corresponding one of the plurality of movement angles of the cervical vertebra corresponding to the one of the plurality of movements of the cervical vertebra, and accumulates a sum of the plurality of movement arc lengths for the plurality of movements of the cervical vertebra acquired during the predetermined measurement period as the movement total amount of the cervical vertebra; and
a notifying unit configured to provide an alarm to a user by sounds or vibrations for prompting that the user needs to move the cervical vertebra when the movement total amount of the cervical vertebra during the predetermined measurement period is less than a predetermined threshold value of the movement amount,
wherein, if a movement angle among the plurality of movement angles of the cervical vertebra is greater than or equal to a valid movement threshold value, the processing unit records the corresponding one of the plurality of movements of the cervical vertebra as a valid movement of the cervical vertebra, and counts the valid movements of the cervical vertebra during the measurement period as a valid movement number of the cervical vertebra.

8. The device as claimed in claim 1, wherein, during a first measurement for the first motion process, the obtaining unit is configured to obtain a plurality of instantaneous first average velocities corresponding to a plurality of time points, obtain an instantaneous first angle of a current time point by multiplying the instantaneous first average velocity of the current time point with a duration from beginning of the first measurement to the current time point, storing an angle whose absolute value is the greatest among a plurality of instantaneous first angles up to the current time point as an instantaneous maximum first angle, update the stored instantaneous maximum first angle with the instantaneous first angle of the current time point only when an absolute value of the instantaneous first angle of the current time point is greater than a previously stored instantaneous maximum first angle, and determine the stored instantaneous maximum first angle as the first angle of the first motion process at end of the first measurement, and during a second measurement for the second motion process, the obtaining unit is configured to obtain a plurality of instantaneous second average velocities corresponding to a plurality of time points, obtain an instantaneous second angle of a current time point by multiplying the instantaneous second average velocity of the current time point with a duration from beginning of the second measurement to the current time point, storing an angle whose absolute value is the greatest among a plurality of instantaneous second angles up to the current time point as an instantaneous maximum second angle, update the stored instantaneous maximum second angle with the instantaneous second angle of the current time point only when an absolute value of the instantaneous second angle of the current time point is greater than a previously stored instantaneous maximum second angle, and determine the stored instantaneous maximum second angle as the second angle of the second motion process at end of the second measurement.

* * * * *